US010765300B2

(12) United States Patent
Kohler et al.

(10) Patent No.: US 10,765,300 B2
(45) Date of Patent: Sep. 8, 2020

(54) ENDOSCOPY DEVICE

(71) Applicant: Scholly Fiberoptic GmbH, Denzlingen (DE)

(72) Inventors: Alexander Kohler, Freiburg (DE); Mathias Hornbach, Waldkirch (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 383 days.

(21) Appl. No.: 15/669,200

(22) Filed: Aug. 4, 2017

(65) Prior Publication Data
US 2018/0035873 A1   Feb. 8, 2018

(30) Foreign Application Priority Data

Aug. 5, 2016   (DE) .................. 10 2016 009 476

(51) Int. Cl.
| | |
|---|---|
| *A61B 1/00* | (2006.01) |
| *H01R 13/658* | (2011.01) |
| *A61B 1/05* | (2006.01) |
| *A61B 1/06* | (2006.01) |

(52) U.S. Cl.
CPC ........ *A61B 1/00114* (2013.01); *A61B 1/0011* (2013.01); *A61B 1/00105* (2013.01); *A61B 1/00124* (2013.01); *A61B 1/05* (2013.01); *A61B 1/0684* (2013.01); *H01R 13/658* (2013.01)

(58) Field of Classification Search
CPC .............. A61B 1/00114; A61B 1/0017; A61B 1/00112; A61B 1/00124; A61B 1/00126; A61B 1/05; A61B 1/051; A61B 1/053; A61B 1/0684; A61B 1/00066; G02B 23/2492; G02B 23/26; H01R 13/658; H01R 13/6581–6589
See application file for complete search history.

(56) References Cited

U.S. PATENT DOCUMENTS

| | | | | |
|---|---|---|---|---|
| 5,170,775 | A * | 12/1992 | Tagami ................. | G02B 23/26 348/75 |
| 5,569,158 | A | 10/1996 | Suzuki et al. | |
| 5,716,323 | A * | 2/1998 | Lee .................... | H04N 5/23203 348/76 |
| 6,099,465 | A * | 8/2000 | Inoue ..................... | A61B 1/05 348/75 |
| 2002/0188176 | A1* | 12/2002 | Kuranishi ............ | A61B 1/0638 600/160 |
| 2009/0048488 | A1* | 2/2009 | Uchimura ............ | A61B 1/0052 600/152 |
| 2009/0287047 | A1* | 11/2009 | Onoda ............... | A61B 1/00009 600/109 |

(Continued)

*Primary Examiner* — Ryan N Henderson
(74) *Attorney, Agent, or Firm* — Volpe and Koenig, P.C.

(57) ABSTRACT

An endoscopy device (1) with an endoscope (2) and a camera control unit (12) is provided. The endoscope (2) has an endoscope shaft (3) and an endoscope head (4), and the endoscope shaft (3) is made of a metallic material. Electronics (8) are arranged in the endoscope head (4) and are connected to an attachment cable (10), and the electronics (8) and the attachment cable (10) are shielded by an electronics shield (14). A galvanic barrier (15) is set up between the electronics shield (14) and the endoscope shaft (3) and couples the endoscope shaft (3) capacitively to the electronics shield (14).

14 Claims, 2 Drawing Sheets

(56) References Cited

U.S. PATENT DOCUMENTS

| | | | |
|---|---|---|---|
| 2012/0209061 A1* | 8/2012 | Kato | A61B 1/00114 600/103 |
| 2013/0150668 A1* | 6/2013 | Kanno | A61B 1/00059 600/109 |
| 2014/0135579 A1* | 5/2014 | Brichard | A61B 1/00004 600/117 |
| 2015/0272426 A1* | 10/2015 | Narita | A61B 1/00124 600/132 |
| 2016/0089000 A1* | 3/2016 | Hara | A61B 1/00016 600/112 |
| 2016/0089001 A1* | 3/2016 | Hara | A61B 1/05 600/109 |
| 2016/0128549 A1* | 5/2016 | Juergens | A61B 1/00112 600/112 |
| 2016/0341952 A1* | 11/2016 | Narita | A61B 1/00124 |
| 2019/0020507 A1* | 1/2019 | Hornbach | H04L 25/0278 |

\* cited by examiner

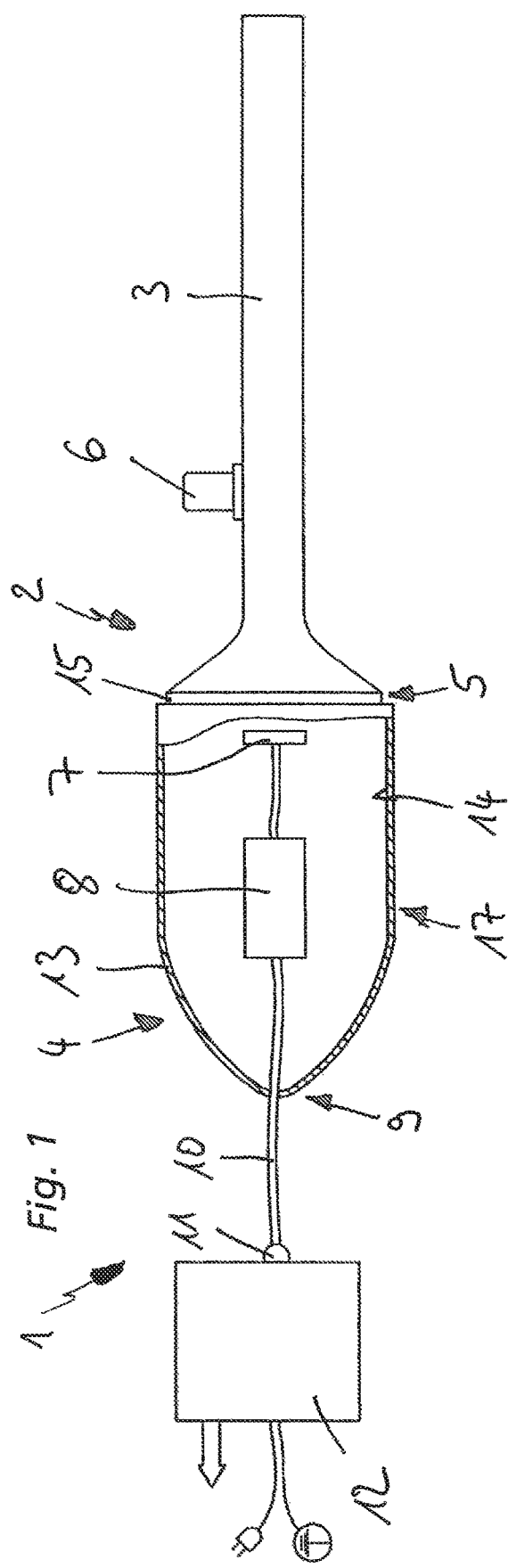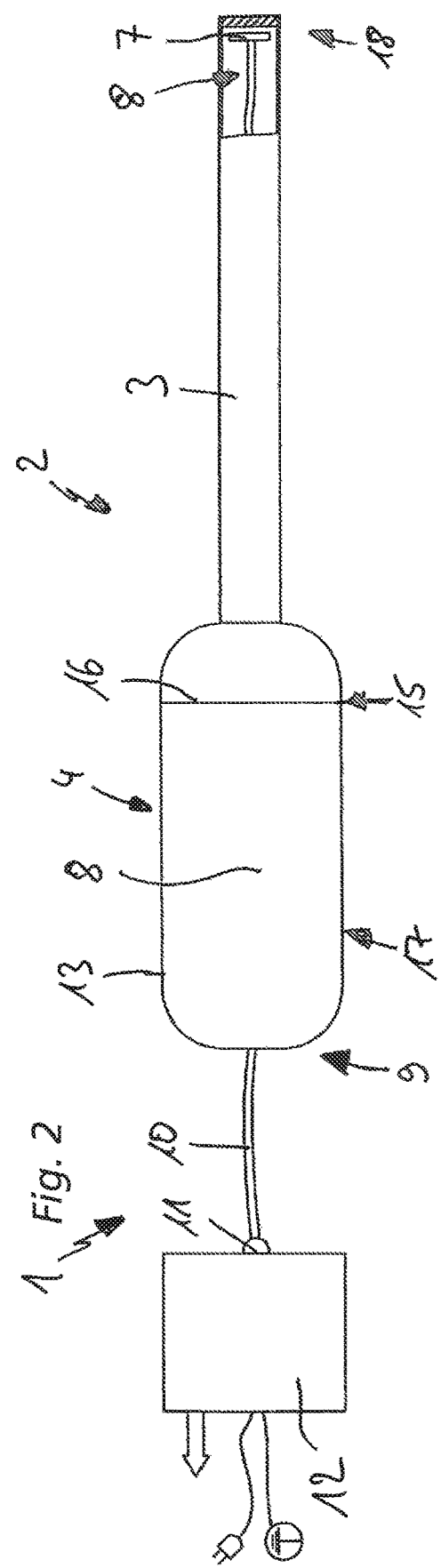

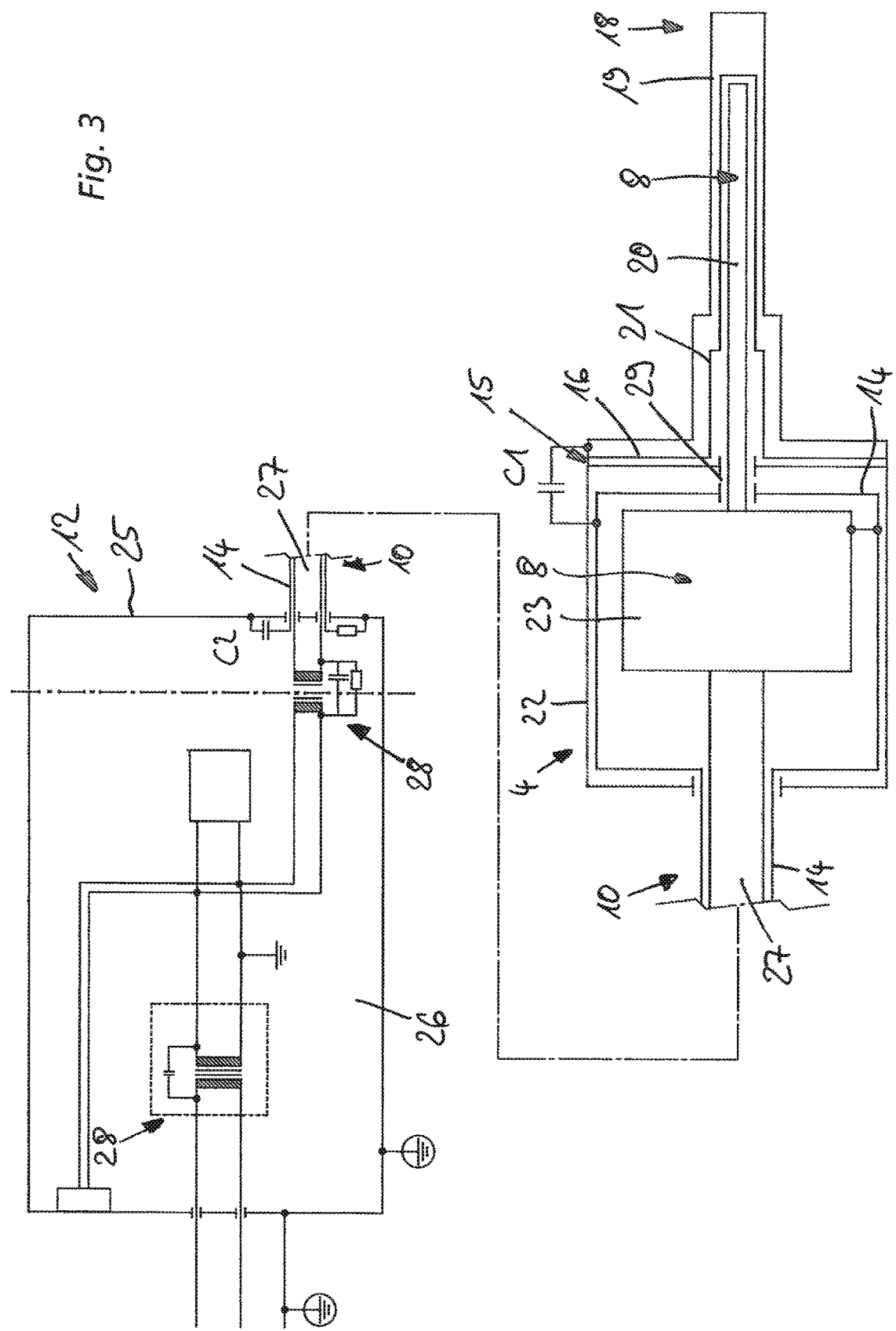

ENDOSCOPY DEVICE

INCORPORATION BY REFERENCE

The following documents are incorporated herein by reference as if fully set forth: German Patent Application No. 102016009476.1, filed Aug. 4, 2016.

BACKGROUND

The invention relates to an endoscope with an endoscope shaft, an endoscope head arranged at a proximal end of the endoscope shaft, and an attachment cable arranged proximally on the endoscope head, wherein electronics are arranged in the endoscope head and the attachment cable has an attachment plug at a proximal end, wherein the electronics are shielded by an electronics shield, wherein the electronics shield also extends in the attachment cable and shields at least one line extending through the attachment cable between the attachment plug and the electronics.

Endoscopes of this kind are known and are attached to a base appliance or stationary appliance, for example a camera control unit, with galvanic isolation being formed in the base appliance in order to protect the patient.

The invention therefore further relates to an endoscopy device with an endoscope and a camera control unit to which an attachment cable of the endoscope is attached.

In order to avoid interference in particular from further surgical instruments arranged near the endoscope during the operation, for example HF (high-frequency) surgical instruments, or from other sources of interference, it has become standard practice to shield the electronics in the endoscope head, with the shield also extending in the attachment cable.

However, there are standard requirements concerning the limitation of leakage currents to the distal end of the endoscope shaft in voltage tests.

SUMMARY

The object of the invention is therefore to enhance the functionality of an endoscope.

The object is achieved by an endoscope with one or more features of the invention. In particular, in an endoscope of the type described at the outset, it is provided according to the invention that the endoscope shaft is made of a metallic material, and that a galvanic barrier is set up between the electronics shield and the endoscope shaft and couples the endoscope shaft capacitively to the electronics shield. Thus, the shielding of the electronics can be closed off distally, in particular in the area of a passage, for an optical or electronic image captured by the endoscope, from the endoscope shaft to the electronics. Here, the barrier can from a shield against interference from outside. In addition, the invention permits the formation of an additional barrier against undesired leakage currents to the endoscope shaft, in order to meet standard specifications.

In one embodiment of the invention, provision can be made that at least one electronics component electrically connected to the electronics is arranged in a distal end of the endoscope shaft. Provision can be made here that the at least one electronics component is shielded with the endoscope shaft. It is thus possible to arrange electronics components in the distal end of the endoscope shaft, such that the electronics components and their attachment lines can be shielded from HF interference. The galvanic barrier causes a reduction of the aforementioned leakage currents to the distal end of the endoscope, such that standard specifications can be met.

In one embodiment of the invention, provision can be made that the at least one electronics component has an image sensor. An endoscope can thus be formed in which a distal or electronic image can be captured at an endoscope tip. The embodiment according to the invention makes it possible to suppress interference caused by adjacent instruments. Alternatively or additionally, provision can be made that the at least one electronics component has a temperature sensor. A temperature measurement can thus be carried out, for example in order to avoid overheating at the endoscope tip. The attachment lines of the temperature sensor act as antennas for the HF interference signals from the environment, which signals may interfere with the capture of an image, for example. The invention can here have the effect that these HF interference signals are suppressed. Alternatively or additionally, provision can be made that the at least one electronics component has a heating element. It is thus possible, for example, to control the temperature of an optical element, for example a protective glass or a lens, at the distal end of the endoscope shaft, particularly with the aid of the aforementioned temperature sensor, in order to prevent or eliminate misting of this optical element.

Alternatively or additionally, provision can be made that the at least one electronics component is a light source, for example at least one LED (light-emitting device). For example, the light source can be attached to the electronics in order to control a switching-on time, an illumination intensity or, generally, to activate the light source.

In the described illustrative embodiments, which can also be combined with one another, the invention has the effect that the attachment lines of the respective at least one electronics component, which extend through the endoscope shaft to or from the electronics, pick up only small interference signals, if indeed any, from adjacent interference sources outside the endoscope shaft.

In one embodiment of the invention, provision can thus be made that the endoscope shaft at least partially shields the at least one electronics component. Additional shielding of the electronics component can thus be omitted.

In one embodiment of the invention, provision can be made that the endoscope shaft is made of a metallic material. It is thereby possible to achieve a high degree of mechanical stability and reprocessability of the endoscope shaft and a shielding of an interior of the endoscope shaft.

An isolation layer is preferably provided between a wall of the endoscope shaft and the at least one electronics component, preferably with associated attachment lines to the electronics. It is thus possible to avoid short-circuits to the endoscope shaft.

In one embodiment of the invention, provision can be made that the endoscope shaft is mechanically separable from the endoscope head at the galvanic barrier. The endoscope shaft is thus exchangeable. This may be advantageous, for example, for reprocessing after use. The embodiment thus combines the barrier according to the invention with a releasable connection. It is thus possible to avoid a weakening of the mechanical stability of the endoscope by the additional barrier.

In one embodiment of the invention, provision can be made that the endoscope head is designed as a handle. This permits easy manipulation of the endoscope. In particular, provision can be made here that the galvanic barrier is formed between a grip area and the endoscope shaft. Thus, a leakage current from the grip area or the adjoining attachment cable to the endoscope tip can be reduced or even completely avoided by the barrier.

In one embodiment of the invention, provision can be made that the galvanic barrier forms a high pass with a limit frequency of below 1 MHz. Interferences above 1 MHz, for example from HF surgery, can thus be avoided. The limit frequency is preferably set at below 1 kHz. This allows HF interference signals to be suppressed particularly efficiently.

In one embodiment of the invention, provision can be made that the galvanic barrier is formed by a film. Provision is preferably made here that the film is arranged between the endoscope shaft and a metal part electrically connected to the electronics shield. A high degree of mechanical stability can thus be obtained on both sides of the film. A high capacitance at the barrier, for good shielding against external interference, can thus be easily obtained if the chosen film is sufficiently thin.

In one embodiment of the invention, provision can be made that the attachment cable has a video line. This has the advantage of permitting wire-bound and shielded transmission of video data or video signals via the attachment cable. The video line is thus part of the aforementioned at least one line of the attachment cable. The video line is preferably a single-core video line, i.e. has just one core. However, it can also have a multi-core configuration. The invention in this case permits particularly good shielding through formation of sufficiently high capacitances, with the barrier according to the invention contributing to meeting the standard specification in respect of maximum leakage currents.

In one embodiment of the invention, provision can be made that the electronics shield has, toward the endoscope shaft, a passage which leads from the electronics to an interior of the endoscope shaft. The passage can in this case serve for guiding an instrument and/or a substance through into the interior. The passage can alternatively or additionally be configured as an electrical and/or optical passage for an attachment line to a distal end of the endoscope shaft and/or for optical transfer of an image captured with the endoscope. This passage, which is technically necessary, and through which interference may enter if there is no shielding, can thus be closed off and shielded from the outside by the invention.

As an alternative or in addition, the aforementioned object is achieved by the additional features described below and in the claims, which are directed to an endoscopy device. In particular, in order to achieve the object in the case of an endoscopy device of the type described in the introduction, it is therefore provided that the endoscopy device be designed with an endoscope according to the invention, in particular as described above and/or according to one of the claims directed to an endoscope, and with a camera control unit to which the attachment cable of the endoscope is attached, wherein the at least one line is galvanically isolated from the camera control unit. An undesired leakage current via the at least one line is avoidable in this way.

In one embodiment of the invention, provision can be made that the electronics shield is coupled capacitively to a housing of the camera control unit. The electronics shield can thus be galvanically isolated from the housing, the electronics shield being able to be connected to the housing in order to shield the at least one line from the outside. Provision is preferably made here that the electronics shield is coupled with a capacitance greater than a capacitance of the galvanic barrier. The invention exploits the fact that the typical interference affecting the capture of an image in the endoscope often stems from immediately adjacent HF surgical instruments, which interference has already substantially subsided in an area surrounding the remotely arranged attachment plug. Thus, the capacitance selected at the attachment plug may be lower, which contributes more effectively to a reduction of the leakage currents in voltage tests or of defects in the camera control unit. By contrast, at the barrier according to the invention, the focus can be directed to the best possible HF shielding, whereas an only small but sufficient contribution to isolation against voltage flashover to the patient can be accepted. The capacitance of the coupling is preferably even at least 100 times greater or even at least 1000 times greater than the capacitance of the barrier. It is thus possible to achieve a good balance between the described influences and effects.

In one embodiment of the invention, provision can be made that the galvanic barrier and a coupling of the electronics shield to the housing form a series connection of capacitors between the housing and the endoscope shaft. It is thus possible for the reductions of the leakage currents at both locations to be added together.

BRIEF DESCRIPTION OF THE DRAWINGS

The invention is now described in more detail on the basis of illustrative embodiments, but it is not limited to these illustrative embodiments. Further illustrative embodiments are obtained through combination of the features of one or several claims with each other and/or with one or several features of the illustrative embodiments.

FIG. 1 shows an endoscopy device according to the invention with an endoscope according to the invention, FIG. 2 shows a further endoscopy device according to the invention with a further endoscope according to the invention, in which an image sensor is arranged in the endoscope shaft, and FIG. 3 shows a schematic circuit diagram of the endoscopy device according to FIG. 2.

DETAILED DESCRIPTION OF THE EMBODIMENTS

FIG. 1 shows an endoscopy device according to the invention designated overall by 1. The endoscopy device 1 has an endoscope 2 according to the invention. The endoscope 2 has an endoscope shaft 3 and an endoscope head 4, which are connected exchangeably to each other via an endoscope coupling 5. The endoscope shaft 3 here is a standard endoscope shaft which can be used with different endoscope heads 4, for example purely optical endoscope heads or endoscope heads equipped with a camera. The endoscope shaft 3 has an attachment piece 6 for an optical waveguide, for attachment to a light source (not shown here).

In the example, the endoscope head 4 is designed as a camera head. An image sensor 7 for capturing images is arranged in the endoscope head 4, in the optical beam path of the endoscope shaft 3. The image sensor 7 is connected to electronics 8, which are connected to an attachment cable 10 guided outward at the proximal end 9 of the endoscope head 4. The attachment cable 10 is attached to a camera control unit 12 (CCU) by a plug-in connector 11.

The endoscope head 4 has a housing 13, which is equipped on the inside with an electronics shield 14, which prevents disturbances caused by incoming or outgoing electromagnetic radiation. The endoscope shaft 3 is made of a metallic material, as a result of which the interior 20 of the endoscope shaft 3 is likewise screened off in respect of electromagnetic radiation. According to the invention, a galvanic barrier 15 is set up between the electronics shield 14 and the endoscope shaft 3 and capacitively couples the endoscope shaft 3 to the electronics shield 14. This on the one hand ensures the shielding and on the other hand provides an additional barrier against undesired leakage currents between the endoscope shaft and the endoscope head, so as to comply with standard specifications.

The galvanic barrier 15 functions more effectively as a shield the greater the capacitance of the capacitive coupling. The galvanic barrier 15 is therefore formed by the film 16 which is arranged between the endoscope shaft 3 and the endoscope head 4, for example at the endoscope coupling 5. The capacitance of the capacitive coupling is then easily adjustable via the material and/or the thickness of the film 16.

FIG. 2 shows a further endoscopy device 1 according to the invention. Here, the endoscope 2 is designed as a video endoscope. In the example, an image sensor 7 and, if appropriate, further electronics 8 are arranged in the distal end 18 of the endoscope shaft 3. The endoscope shaft 3 here is also made of a metallic material and therefore already provides an electronics shield by itself.

Here, the endoscope head 4 likewise has further electronics 8, which are connected to a CCU 12 via an attachment cable 10 in a manner analogous to the endoscope 2 of FIG. 1. The endoscope shaft 3 and the endoscope head 4 are also connected to each other via an endoscope coupling 5 in this embodiment.

The endoscope head 4 has an electronics shield 14, which is connected to the endoscope shaft 3 via a galvanic barrier 15. For this purpose, a film 16 for the capacitive coupling is arranged at the endoscope coupling 5.

FIG. 3 shows a schematic circuit diagram of an endoscopy device 1 according to FIG. 2 with an endoscope 2 and a camera control unit 12.

The schematic circuit diagram shows the endoscope shaft 3 with a wall 19, which delimits an interior 20 in which electronics components 8 are arranged, for example an image sensor, a temperature sensor and/or further components, for example a light source. An isolation layer 21 is arranged between the wall 19 and the electronics components 8 in order to avoid short-circuits. The wall 19 of the endoscope shaft 3 is made of a metallic material, such that it acts as an electromagnetic shield.

The endoscope head 4 likewise has a wall 22, which delimits an interior 23 in which electronics components 8 are arranged. In the interior 23 of the endoscope head 4, an electronics shield 14 is arranged around the electronics components 8. There is no conductive electrical connection between the electronics shield 14 and the wall 19 of the endoscope shaft 3. Instead, a film 16 forms a galvanic barrier 15 by capacitive coupling, which is represented in the circuit diagram by the capacitor C1.

The electronics shield 14 has, toward the endoscope shaft 3, a preferably electrical and/or optical passage 29, which leads from the electronics to an interior 20 of the endoscope shaft 3.

The endoscope head 4 is connected to a camera control unit 12 via an attachment cable 10. The electronics shield 14 also extends onto the attachment cable 10, such that an attachment line 27 extending in the attachment cable 10 is also shielded by the electronics shield 14.

The camera control unit 12 has a housing 25 made of a metallic material and delimiting an interior 26 in which electronics components 8 are arranged. The wall 25 also acts here as an electronics shield for the interior 26.

The shield 14 of the attachment cable 10 is capacitively coupled to the housing 25, as is indicated by the capacitor C2. The capacitor C2 preferably has a greater capacitance than the capacitor C1, particularly preferably more than 100 times the capacitance or more than 1000 times or 10000 times the capacitance, for example 10 nF, while C1 can lie below 1 pF. However, the attachment line 27 of the attachment cable 10 is connected to the electronics 8 via a galvanic isolation 28, for example by an optocoupler or transformer.

FIG. 3 shows an endoscopy device 1 with an endoscope 2 and a camera control unit 12, wherein the endoscope 2 has an endoscope shaft 3 and an endoscope head 4, wherein the endoscope shaft 3 is made of a metallic material, wherein electronics 8 are arranged in the endoscope head 4 and are connected to an attachment cable 10, wherein the electronics 8 and the attachment cable 10 are shielded by an electronics shield 14, and wherein a galvanic barrier 15 is set up between the electronics shield 14 and the endoscope shaft 3 and couples the endoscope shaft 3 capacitively to the electronics shield 14.

In an endoscope 2, it is thus provided to configure a galvanic barrier 15 between an endoscope shaft 3 and an endoscope head 4, which galvanic barrier 15 couples the endoscope shaft 3 capacitively to an electronics shield 14 of the endoscope head 4 in order to shield electronics 8 from interference signals caused in particular by HF surgical instruments in an environment of the endoscope 2.

LIST OF REFERENCE SIGNS 1 endoscopy device
2 endoscope
3 endoscope shaft
4 endoscope head
5 endoscope coupling
6 attachment piece for optical waveguide
7 image sensor
8 electronics
9 proximal end of the endoscope head
10 attachment cable
11 plug
12 camera control unit (CCU)
13 housing of the endoscope head
14 electronics shield
15 galvanic barrier
16 film
17 grip area
18 distal end of the endoscope shaft
19 wall of the endoscope shaft
20 interior of the endoscope shaft
21 isolation layer
22 wall of the endoscope head
23 interior of the endoscope head
25 housing of the CCU
26 interior of the CCU
27 attachment line
28 galvanic isolation
29 passage
C1 capacitance between endoscope shaft and endoscope head
C2 capacitance between attachment cable and CCU

The invention claimed is:

1. An endoscope (2) comprising: an endoscope shaft (3), an endoscope head (4) arranged at a proximal end of the endoscope shaft (3), an attachment cable (10) arranged proximally on the endoscope head (4), electronics (8)

arranged in the endoscope head (4), an attachment plug (11) at a proximal end of the attachment cable (10), an electronics shield (14) that shields the electronics (8), wherein the electronics shield (14) also extends in the attachment cable (10) and shields at least one line (27) extending through the attachment cable (10) between the attachment plug (11) and the electronics (8), the endoscope shaft (3) is made of a metallic material, a galvanic barrier (15) is disposed between the electronics shield (14) and the endoscope shaft (3) and couples the endoscope shaft (3) capacitively to the electronics shield (14), and the endoscope shaft (3) is mechanically separable from the endoscope head at the galvanic barrier (15).

2. The endoscope (2) as claimed in claim 1, wherein at least one electronics component is electrically connected to the electronics (8) and is arranged in a distal end of the endoscope shaft (3), and the endoscope shaft (3) acts as a shield for the at least one electronics component (8).

3. The endoscope (2) as claimed in claim 2, wherein the at least one electronics component includes at least one of an image sensor (7), a temperature sensor or a heating element.

4. The endoscope (2) as claimed in claim 2, further comprising an isolation layer (21) provided between a wall (19) of the endoscope shaft (3) and the at least one electronics component.

5. The endoscope (2) as claimed in claim 1, wherein the endoscope head (4) is designed as a handle, and the galvanic barrier (15) is formed between a grip area (17) and the endoscope shaft (3).

6. The endoscope (2) as claimed in claim 1, wherein the galvanic barrier (15) forms a high pass filter that limits a frequency of below 1 MHz to be transmitted therethrough.

7. The endoscope (2) as claimed in claim 1, wherein the galvanic barrier (15) is formed by a film (16).

8. The endoscope (2) as claimed in claim 7, wherein the film (16) is between the endoscope shaft (3) and a metal part electrically connected to the electronics shield (14).

9. The endoscope (2) as claimed in claim 1, wherein the attachment cable (10) has a video line.

10. The endoscope (2) as claimed in claim 1, wherein the electronics shield (14) has, toward the endoscope shaft (3), an at least one of electrical or optical passage (29) which leads from the electronics to an interior of the endoscope shaft (3).

11. An endoscopy device (1) comprising an endoscope (2) as claimed in claim 1, and a camera control unit (12) to which the attachment cable (10) is attached, wherein the at least one line (27) is galvanically isolated from the camera control unit (12).

12. The endoscopy device (1) as claimed in claim 11, wherein the electronics shield (14) is coupled capacitively to a housing (25) of the camera control unit (12).

13. The endoscopy device (1) as claimed in claim 12, wherein the electronics shield (14) is coupled capacitively to the housing (25) of the camera control unit (12) with a capacitance (C2) greater than a capacitance (C1) of the galvanic barrier (15).

14. The endoscopy device (1) as claimed in claim 11, wherein the galvanic barrier (15) and a coupling of the electronics shield (14) to a housing (25) form a series connection of capacitors between the housing (25) and the endoscope shaft (3).

* * * * *